(12) United States Patent
    Lord et al.

(10) Patent No.:    US 12,593,978 B2
(45) Date of Patent:      Apr. 7, 2026

(54) SYSTEM AND METHOD FOR IDENTIFYING A DISEASE AFFECTED AREA

(71) Applicant: Disease Advisor Pty Ltd, Albany Creek (AU)

(72) Inventors: Anton Lord, Albany Creek (AU); Maggy Lord, Albany Creek (AU)

( * ) Notice: Subject to any disclaimer, the term of this patent is extended or adjusted under 35 U.S.C. 154(b) by 791 days.

(21) Appl. No.: 17/766,150

(22) PCT Filed: Oct. 2, 2020

(86) PCT No.: PCT/AU2020/051061
§ 371 (c)(1),
(2) Date: Apr. 1, 2022

(87) PCT Pub. No.: WO2021/062484
PCT Pub. Date: Apr. 8, 2021

(65) Prior Publication Data
US 2022/0369925 A1     Nov. 24, 2022

(30) Foreign Application Priority Data
Oct. 4, 2019    (AU) ................................. 2019903741

(51) Int. Cl.
*G16H 50/30*      (2018.01)
*A61B 5/00*      (2006.01)
      (Continued)

(52) U.S. Cl.
CPC ........ *A61B 5/0004* (2013.01); *A61B 2576/00* (2013.01)

(58) Field of Classification Search
None
See application file for complete search history.

(56) References Cited

U.S. PATENT DOCUMENTS

| | | | |
|---|---|---|---|
| 10,366,791 | B1 | 7/2019 | Thiagarajan |
| 2007/0229290 | A1 | 10/2007 | Kahn |

(Continued)

FOREIGN PATENT DOCUMENTS

| | | | | |
|---|---|---|---|---|
| JP | 2014186447 | * 10/2014 | ............. | G06Q 50/22 |
| KR | 20110131363 | * 12/2011 | ............. | H04W 4/02 |

(Continued)

OTHER PUBLICATIONS

International Search Report and Written Opinion of International Searching Authority corresponding to International Patent Application No. PCT/AU2020/051061, mailed Dec. 11, 2020 (12 pages).

(Continued)

*Primary Examiner* — Beniyam Menberu

(57) ABSTRACT

A method for identifying a disease affected area. The method includes activating a geolocation device of an electronic communication device, determining a current geolocation from the geolocation device, querying a disease database from the electronic communication device, to identify one or more diseases associated with the current geolocation, and generating a graphical display on a display of the electronic communication device displaying a risk rating associated with each of the one or more identified diseases associated with the current geolocation.

13 Claims, 8 Drawing Sheets

(51) Int. Cl.
G16H 50/80 (2018.01)
H04W 4/029 (2018.01)

(56) References Cited

U.S. PATENT DOCUMENTS

| | | | |
|---|---|---|---|
| 2012/0112883 A1* | 5/2012 | Wallace | G16H 50/80 |
| | | | 340/10.1 |
| 2012/0123806 A1 | 5/2012 | Schumann, Jr. | |
| 2013/0226948 A1 | 8/2013 | Ahn | |
| 2015/0379240 A1 | 12/2015 | Blom | |
| 2016/0140311 A1 | 5/2016 | Pastore et al. | |
| 2017/0161617 A1 | 6/2017 | Avegliano et al. | |
| 2017/0351831 A1 | 12/2017 | Cahan | |
| 2018/0310890 A1* | 11/2018 | Li | A61B 5/4842 |

FOREIGN PATENT DOCUMENTS

| | | | |
|---|---|---|---|
| WO | WO 2017/080500 A1 | 5/2017 | |
| WO | 2019020744 A1 | 1/2019 | |

OTHER PUBLICATIONS

India First Exam Report issued for corresponding Application No. 202247023617 mailed Mar. 18, 2025.

* cited by examiner

FIG 6.

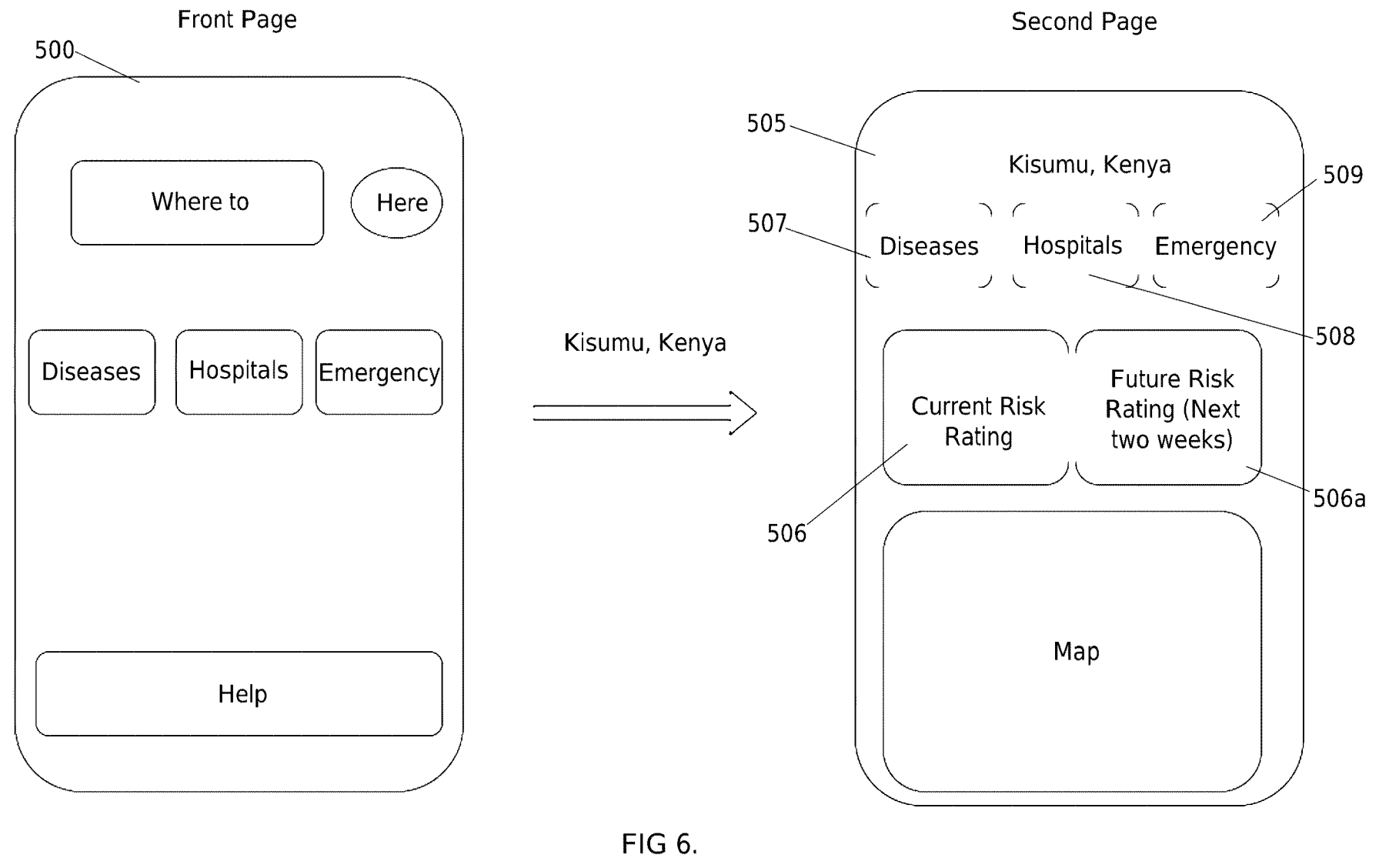

Second Page

Kisumu, Kenya

Diseases    Hospitals    Emergency

509

508

505

507

Current Risk Rating

Future Risk Rating (Next two weeks)

506a

506

Map

Kisumu, Kenya

Front Page

Here

Where to

Diseases    Hospitals    Emergency

Help

500

SYSTEM AND METHOD FOR IDENTIFYING A DISEASE AFFECTED AREA

CROSS-REFERENCE TO RELATED APPLICATIONS

This application is a U.S. National Stage of International Application No. PCT/AU2020/051061, filed Oct. 2, 2020, which claims the benefit of Australian Patent Application No. 2019903741, filed Oct. 4, 2019, both of which are incorporated herein by reference in their entireties.

FIELD

The present disclosure relates to systems and methods for risk advisory. In particular, the present disclosure relates to system and methods for identifying a disease affected area or area at risk of natural disasters.

BACKGROUND

Any references to method, apparatus or documents of the prior are not to be taken as constituting any evidence or admission that they formed, or form, part of the common general knowledge.

More than half of the world's population live in areas endemic with infectious disease. As international and local travel becomes more accessible, the risk of exposure to potentially harmful pathogens increases. As a result, people from countries/regions that are free from a particular infectious disease, may become exposed during travels but not suffer any ill effects or develop symptoms until much later when they return to their home country/region or the next destination country/region and act as a source for an outbreak. This presents problems in identifying, controlling and eliminating potentially highly infectious diseases and also for medical practitioners in diagnosing and treating symptoms.

OBJECT

It is an aim of this disclosure to provide a system and/or method for identifying a high risk environment such as a disease affected area or an area susceptible to natural disasters which overcomes or ameliorates one or more of the disadvantages or problems described above, or which at least provides a useful commercial alternative.

Other preferred objects of the present invention will become apparent from the following description.

SUMMARY OF THE INVENTION

A method for identifying a disease affected area, the method comprising the steps of:

activating a geolocation device of an electronic communication device;

determining a current geolocation from the geolocation device;

querying a disease database from the electronic communication device, to identify one or more diseases associated with the current geolocation; and generating a graphical display on a display of the electronic communication device displaying a risk rating associated with each of the one or more identified diseases associated with the current geolocation.

A system for identifying a disease affected area, the system comprising:

a disease database storing disease data associated with one or more geolocations;

an electronic communication device adapted for communication with the disease database, the electronic communication device having a display and a geolocation device for determining a current geolocation of the electronic communication device;

wherein upon detecting the current geolocation of the electronic communication device, the electronic communication queries the disease database to identify one or more diseases associated with the current geolocation and display a risk rating associated with each of the one or more identified diseases associated with the current geolocation of the electronic communication device on the display of the electronic communication device.

Preferably, the disease database is configured to receive, process and store disease data for one or more geolocations from one or more sources. Preferably, the one or more sources include: pre-calculated risk maps and time stamped global positioning system (GPS) coordinate data. Preferably, the disease database generates georeferenced risk maps from the disease data for one or more geolocations.

Preferably, the geolocation is determined by a GPS module in the electronic communication device or by a mobile phone tracking process and transmitted as geolocation data. Preferably, the mobile phone tracking process comprises a triangulation process.

Preferably, the disease data comprises a risk rating for each of one or more diseases associated with one or more geolocations. Preferably, the disease database calculates the risk rating for each of one or more diseases associated with one or more geolocations.

Preferably, the geolocation data obtained by the GPS module in relation to the current geolocation and the disease data are combined and compared with incubation periods for diseases present in the current geolocation area to predict the risk of illness being caused by each of the identified diseases associated with the current geolocation.

Preferably, the disease database is remote from the electronic communication device or stored on the electronic communication device.

Preferably, the graphical display comprises a push notification or text message displayed on the display of the electronic communication device. Preferably, the push notification comprises the risk rating for each of the one or more identified diseases associated with the current geolocation.

Preferably, after determining the current geolocation, the method further comprises the step of determining an updated geolocation of the electronic communication device at predetermined intervals;

querying the disease database from the electronic communication device at each predetermined interval, to identify one or more diseases associated with the updated geolocation; and generating a graphical display on a display of the electronic communication device displaying a risk rating for each of the one or more identified disease risk ratings associated with the updated geolocation.

Preferably, the risk rating may comprise a current risk rating and a future risk rating. Preferably, the future risk rating relates to a risk of transmission or infection in a predetermined period of time from a current time. Preferably, the future risk rating is calculated from a predictive model. Preferably, the predictive model incorporates supplementary data (e.g. weather data or rainfall data, temperature data and movement of people) to predict future risk of transmission or infection in the current geolocation.

Preferably, the method further comprises the step of transmitting geolocation data and/or symptom data from the electronic communication device to a second electronic communication device.

Preferably, the method further comprises the step of establishing an open-communication channel with the second electronic communication device. Preferably, the open-communication channel comprises a two-way communication channel allowing the electronic communication device and the second electronic communication device to send and receive data from the other device.

Preferably, the method further comprises the step of determining one or more disease infected vectors based on the geolocation of the electronic communication device.

Preferably, the geolocation data comprises the current geolocation and/or one or more previous/historic geolocations of the electronic communication device determined by the geolocation device of the electronic communication device.

Preferably, the electronic communication device comprises a smartphone.

Preferably, the geolocation device comprises a Global Positioning System (GPS) receiver or transceiver installed in the electronic communication device.

A method for identifying a high-risk environment, the method comprising the steps of:

activating a geolocation device of an electronic communication device;

determining a current geolocation from the geolocation device;

querying an environment database from the electronic communication device, to identify one or more environmental phenomena associated with the current geolocation; and generating a graphical display on a display of the electronic communication device displaying a risk rating associated with each of the one or more identified environmental phenomena associated with the current geolocation.

A system for identifying a high-risk environment, the system comprising:

an environment database storing environment data associated with one or more geolocations;

an electronic communication device adapted for communication with the environment database, the electronic communication device having a display and a geolocation device for determining a current geolocation of the electronic communication device;

wherein upon detecting the current geolocation of the electronic communication device, the electronic communication queries the environment database to identify one or more environmental phenomena associated with the current geolocation and display a risk rating associated with each of the one or more identified environmental phenomena associated with the current geolocation of the electronic communication device on the display of the electronic communication device.

Preferably, the environmental phenomena comprises a natural disaster.

Further features and advantages of the present invention will become apparent from the following detailed description.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way.

By way of example only, preferred embodiments of the invention will be described more fully hereinafter with reference to the accompanying figures, wherein:

FIG. 4a illustrates the use of the smartphone to communicate with a second smartphone to provide symptom information to a GP or the like;

FIG. 6 illustrates a screen displayed on the smartphone according to another embodiment of the invention.

DETAILED DESCRIPTION OF THE
PREFERRED EMBODIMENTS

The present disclosure provides a system and method for risk advisory in relation to infectious diseases that are prevalent in a particular geographical area or geolocation. The disclosure also provides a system and method for risk advisory in relation to high-risk environments that are subject to environmental phenomena, such as natural disasters.

The term "geolocation" has been used interchangeably with the term "location" throughout the present disclosure.

Figure 1:
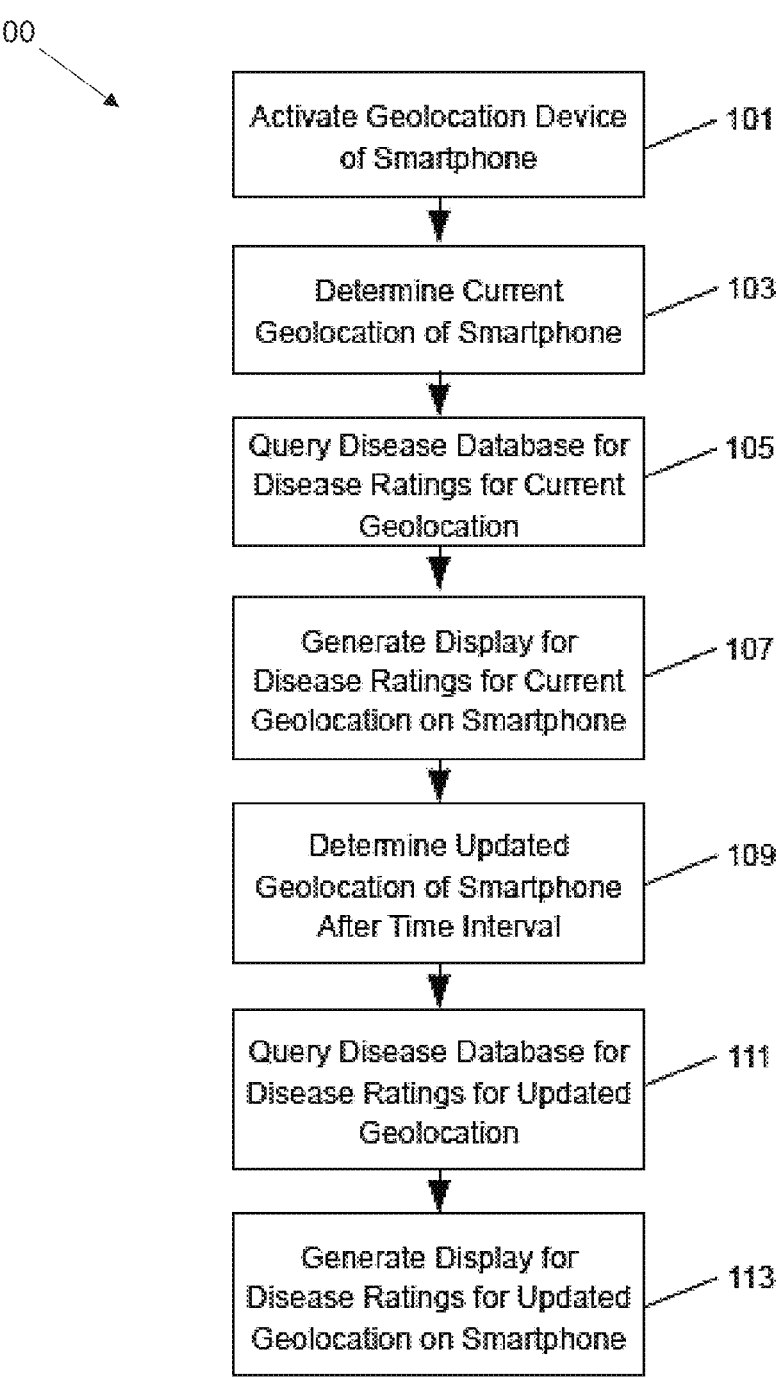
FIG. 1 is a flowchart illustrating a method for identifying a disease affected area.
Figure 2:
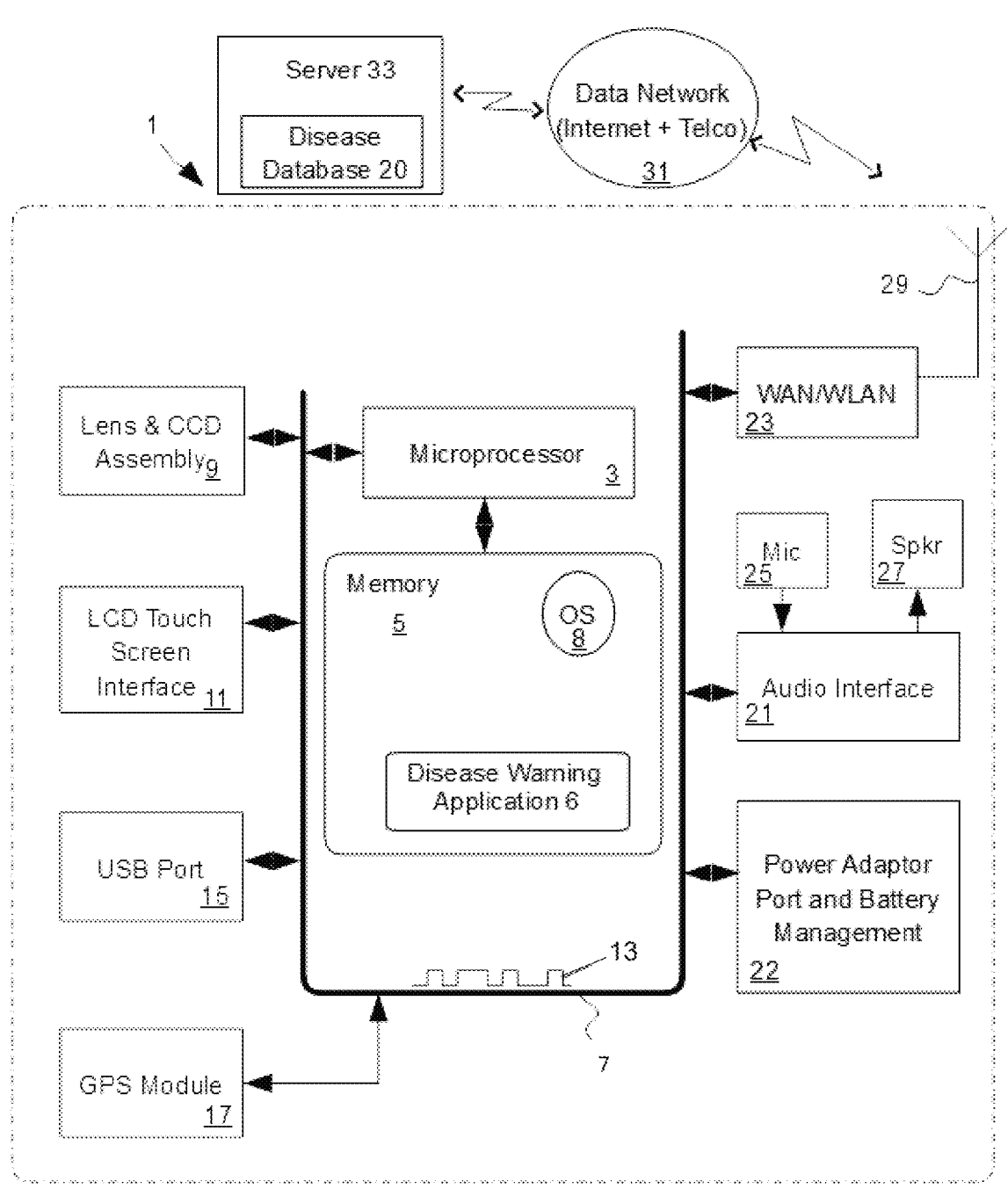
FIG. 2 is a block diagram of a specially configured and programmed computational apparatus in the form of a smartphone that is specially programmed to identify a disease affected area.

With reference to FIGS. 1 and 2, there is shown a flow chart 100 and specially configured computational apparatus in the form of a smartphone 1 which is specially configured and programmed for identifying a disease affected area according to an exemplary embodiment.

Referring specifically to FIG. 2 first, a block diagram of smartphone 1 having a unique combination of software and hardware is shown. Smartphone 1 comprises one or more processors in the form of microprocessor 3 and an electronic memory 5 that is accessible to the microprocessor 3 and which stores instructions comprising a disease warning app 6 that are executable by the microprocessor 3 in order for the smartphone 1 to determine the presence of disease as well as a risk of disease in a particular location or geographical area. Disease warning app 6 can also be adapted to identify high-risk areas that have been the subject of environmental phenomena (i.e. natural disasters).

The electronic memory 5 includes an operating system 8 such as the Android operating system or the Apple IOS operating system, for example, for execution by the microprocessor 3. The electronic memory 5 stores the disease warning application 6 which includes instructions for microprocessor 3 to activate the GPS module 17 to determine a current geolocation and communicate with a remote server 33, as will be explained.

The microprocessor 3 is in data communication with a plurality of peripheral assemblies 9 to 23, as indicated in FIG. 2, via a data bus 7. The peripheral assemblies include a Lens & CCD Assembly 9, an LCD Touch Screen Interface 11, a USB Port 15, GPS Module 17, Microphone 25, Speaker 27, Audio Interface 21 and Power Adaptor Port and Battery Management 22.

The data bus 7 consists of metal tracks which convey electrical data signals 13 between the various assemblies of the device 1. The smartphone 1 is able to establish voice and data communication with a voice and/or data communications network 31 via WAN/WLAN assembly 23 and radio frequency antenna 29 and so is able to transmit the geolocation data (which consists of geographical coordinates) to server 33.

Figure 3:
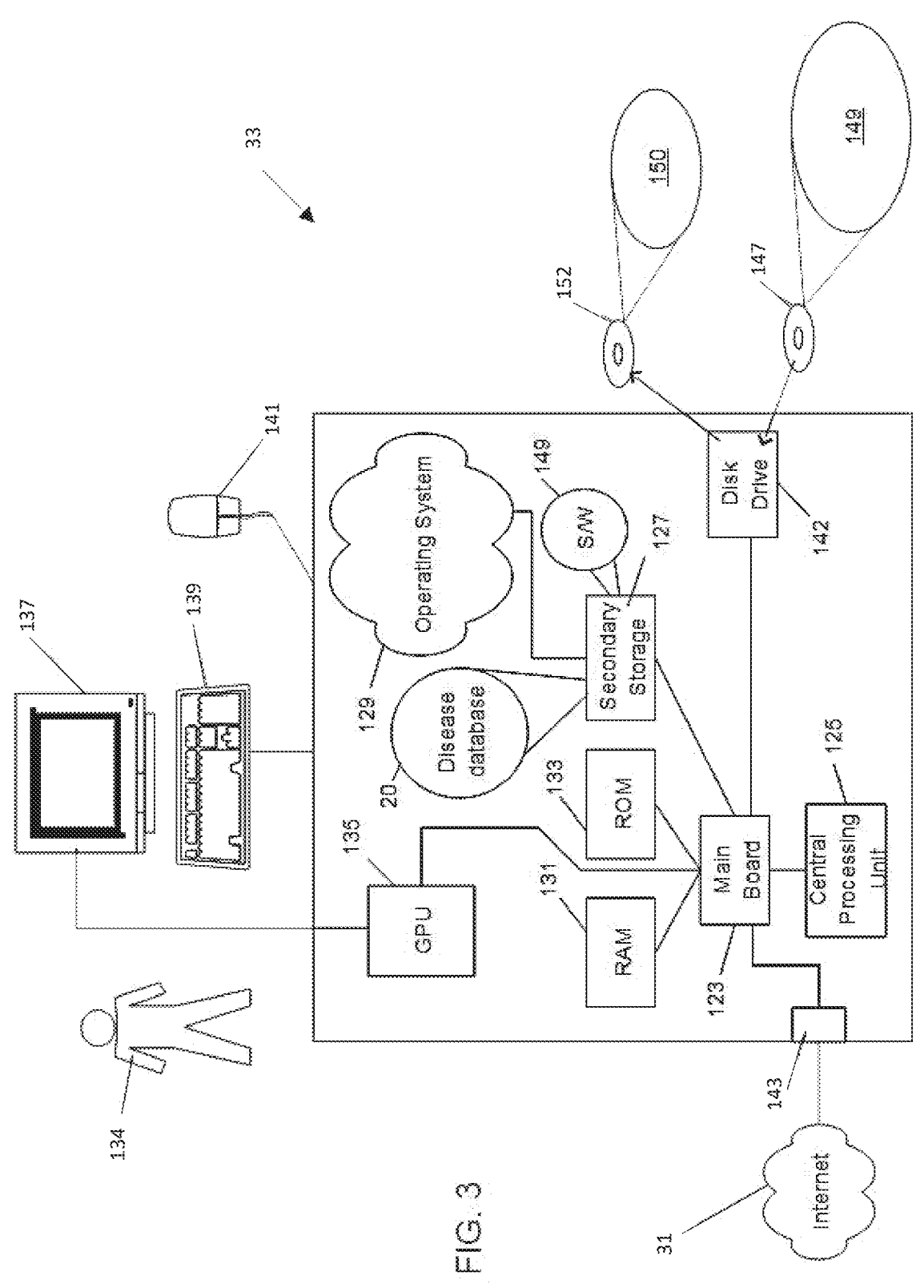
FIG. 3 is a block diagram of a computational apparatus in the form of a computer server that is specially programmed to process and store disease data that is accessed by the smartphone.

FIG. 3 is a block diagram of an exemplary computer server 33 for carrying out a method according to an embodiment of the invention, such as method 100 mentioned above.

The computer system 33 includes a main board 123 which includes circuitry for powering and interfacing to at least one on-board Central Processing Unit (CPU) 125. The one or more on-board processor(s) 125 may comprise two or more discrete processors or processors with multiple processing cores.

The main board 123 acts as an interface between CPU 125 and secondary memory storage 127. The secondary memory 127 may comprise one or more optical or magnetic, or solid state, drives. The secondary memory 127 stores instructions for an operating system 129. The main board 123 includes busses by which the CPU is able to communicate with random access memory (RAM) 131, read only memory (ROM) 133 and various peripheral circuits. The ROM 133 typically stores instructions for a Basic Input Output System (BIOS) which the CPU 125 accesses upon start up and which preps the CPU 125 for loading of the operating system 129.

The main board 123 also interfaces with a graphics processor unit (GPU) 135. It will be understood that in some systems the graphics processor unit 135 is integrated into the main board 123. The GPU 135 drives a display 137 which includes a rectangular screen comprising an array of pixels.

The main board 123 will typically include a communications adapter, for example a LAN adaptor or a modem, either wired or wireless, that is able to put the computer system 121 in data communication with a computer network such as the Internet 31 via port 143.

A user 134 of the computer system 121 may interface with it by means of keyboard 139, mouse 141 and the display 137.

The server 33 automatically, via programming, commands the operating system 129 to load software product 149 which contains instructions for the server 33 to perform disease risk analysis procedures on the current geolocation data that is received from the smartphone 1 and to generate a risk rating for diseases associated with the current geolocation indicated by the current geolocation data and the disease database 20, which will be explained in more detail below. The software product 149, 150 may be provided as tangible instructions borne upon a computer readable media such as optical disk 147, 152 for reading by disk reader/writer 142. Alternatively it might also be downloaded via port 143 from a remote data source via data network 31. Software 149 also includes instructions for establishing a disease database 20 in secondary storage 127, which includes all of the disease data, or alternatively the disease data may be stored in another data storage arrangement that is accessible to server 33 or downloaded from the disease database 20 onto the smartphone 1.

Data collected and stored in disease database 20 includes pre-calculated risk maps, time stamped GPS coordinate data describing confirmed disease cases, supplementary information about diseases including symptoms, vector information (e.g. species, biting habits etc.), name, location and contact details of hospitals and pharmacies, local emergency contact numbers, and embassy information (e.g. name, location and contact details of an embassy or ambassador).

Known sources of data including risk maps from published literature, updates from reputable government or non-government agencies and databases which are updated regularly are also incorporated into the disease database 20 and server 33 in an automated manner. Time limited safety information (e.g. disease outbreaks or natural disasters) may also be incorporated into the risk maps from similar data sources.

Updated disease data will be pulled from the known data sources and incorporated into server 33 and disease database 20 to provide up-to-date disease information to users. This server 33 may then push updates to the smartphone 1 whenever they are available, and the user agrees. Data stored on the smartphone 1 will be available to be used with or without connection to the internet and the users' location can be identified using the mobile phone's GPS.

Risk ratings or statistics for disease at a location are derived by either developing geofenced zones for each disease based on pre-calculated maps and/or GPS point information or by co-locating specific GPS coordinates against pre-calculated risk maps directly.

In use, disease database 20 uses georeferenced risk maps which are compared with the current geolocation data provided as GPS co-ordinate information from where the end user having smartphone 1 currently is to identify and report which diseases are present for that location. In some embodiments, a selected location (e.g. a searched location) may also be assessed.

Disease database 20 may also access (from known sources) and store information relating to a number of diseases, including causes, symptoms and methods of prevention associated with each disease.

In an alternative embodiment, the server 33 automatically, via programming, commands the operating system 129 to load software product 149 which contains instructions for the server 33 to perform risk analysis procedures on the current geolocation data that is received from the smartphone 1 and to generate a risk rating for the location based on environmental phenomena (such as natural disasters, for example) associated with the current geolocation indicated by the current geolocation data and an environmental phenomena database (not shown), which will be explained in more detail below.

As described above in relation to the first embodiment, the software product 149 may be provided as tangible instructions borne upon a computer readable media such as optical disk 147 for reading by disk reader/writer 142. Alternatively it might also be downloaded via port 143 from a remote data source via data network 31. Software 149 also includes instructions for establishing an environmental phenomena database in secondary storage 127, which includes all of the disease data, or alternatively the disease data may be stored in another data storage arrangement that is accessible to server 33 or downloaded from the environmental phenomena database onto the smartphone 1.

Data collected and stored in an environmental phenomena database includes pre-calculated risk maps, time stamped GPS coordinate data describing confirmed disasters and/or other phenomena, supplementary information about phenomena and/or natural disasters, name, location and contact details of hospitals and pharmacies, local emergency contact numbers, and embassy information (e.g. name, location and contact details of an embassy or ambassador).

Known sources of data including risk maps from published literature, updates from reputable government or non-government agencies and databases which are updated regularly are also incorporated into the environmental phenomena database and server 33 in an automated manner. Time limited safety information (e.g. natural disasters) may also be incorporated into the risk maps from similar data sources.

Updated data will be pulled from the known data sources and incorporated into server 33 and environmental phenomena database to provide up-to-date disaster and phenomena information to users. This server 33 may then push updates to the smartphone 1 whenever they are available, and the user agrees. Data stored on the smartphone 1 will be available to be used with or without connection to the internet and the users' location can be identified using the mobile phone's GPS.

Risk ratings or statistics for a high-risk environment subject to environmental phenomena or natural disasters at a location are derived by either developing geofenced zones for each phenomenon based on pre-calculated maps and/or GPS point information or by co-locating specific GPS coordinates against pre-calculated risk maps directly.

In use, the environmental phenomena database uses geo-referenced risk maps which are compared with the current geolocation data provided as GPS co-ordinate information from where the end user having smartphone 1 currently is to identify and report which disasters are present for that location. In some embodiments, a selected location (e.g. a searched location) may also be assessed.

The environmental phenomena database may also access (from known sources) and store information relating to a number of disasters, including type of disaster, current state (e.g. ongoing, under control, being monitored, etc).

Referring to FIG. 1, at box 101 a geolocation device in the form of a Global Positioning System (GPS) Module (such as GPS Module 17 of smartphone 1, for example) is activated.

At box 103 the smartphone determines the current geolocation of the smartphone using the GPS module and saves this geolocation data. While the operations described in relation to boxes 101 and 103 describes determining a geolocation and geolocation data from a GPS module of the smartphone 1, it will be appreciated that some embodiments may use a known mobile phone tracking process, such as cell tower triangulation which determines a mobile phone's approximate location based on the phone's signal strength to nearby antenna masts.

At box 105 the smartphone queries the disease database, either by wirelessly transmitting the current geolocation data to a remotely located disease database or by accessing a disease database stored locally on the smartphone (this may have been pre-loaded or downloaded earlier by the user) to identify and report which diseases are present for that location. At box 107 the smartphone generates a display showing the diseases known to be affecting that area and provides disease ratings or risks for the identified diseases that are present or prevalent in the current location as indicated by the current geolocation data.

In some preferable embodiments, at box 109 the smartphone determines an updated geolocation of the smartphone using the GPS module and saves this updated geolocation data. The smartphone may be programmed to determine the updated geolocation after a predetermined time interval (e.g.

24 hours), as indicated in FIG. 1. However, in some embodiments the smartphone may also be programmed to determine the updated geolocation based on detected movement of the smartphone through one or more sensors present in the smartphone, such as a gyroscope, magnetometer and/or accelerometer.

At box 111 the smartphone queries the disease database with the updated geolocation data in the same manner as described above in relation to box 105.

At box 113 the smartphone generates an updated display for disease ratings or risks for the diseases identified as present or prevalent in the new location as indicated by the updated geolocation data.

Figure 4:
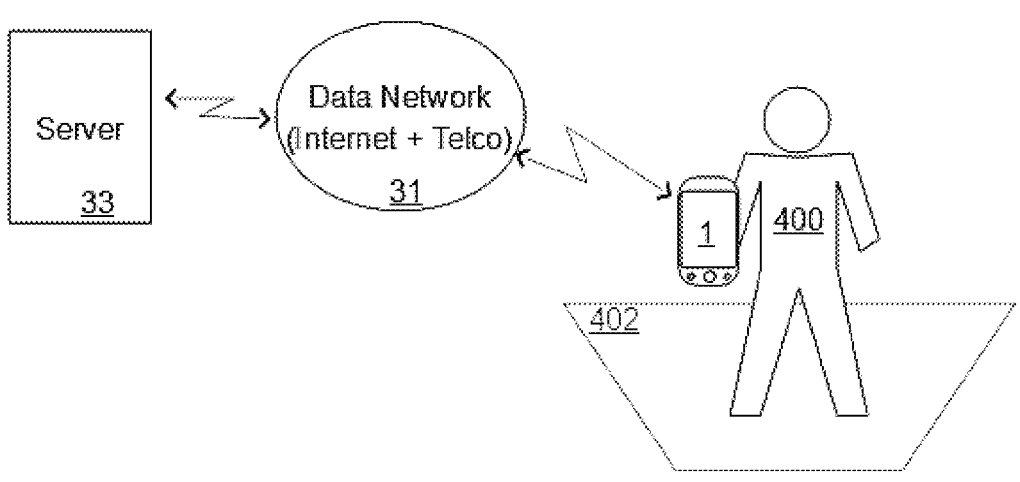
FIG. 4 illustrates the use of the smartphone that is specially programmed to identify a disease affected area.

Referring now to FIG. 4, in use, a traveller 400 arrives at location 402, which may be a country, a state, a city or a suburb, or some other geographical area defined within the disease database. The traveller 400 activates the disease warning application 6 installed on smartphone 1. The disease warning application 6 then activates the GPS module of the smartphone 1 and performs the steps described above in relation to method 100. While throughout this disclosure there is reference to an application installed on a smartphone, the method may be embodied by a website or web application accessed through a browser on a smartphone.

Figure 5A:
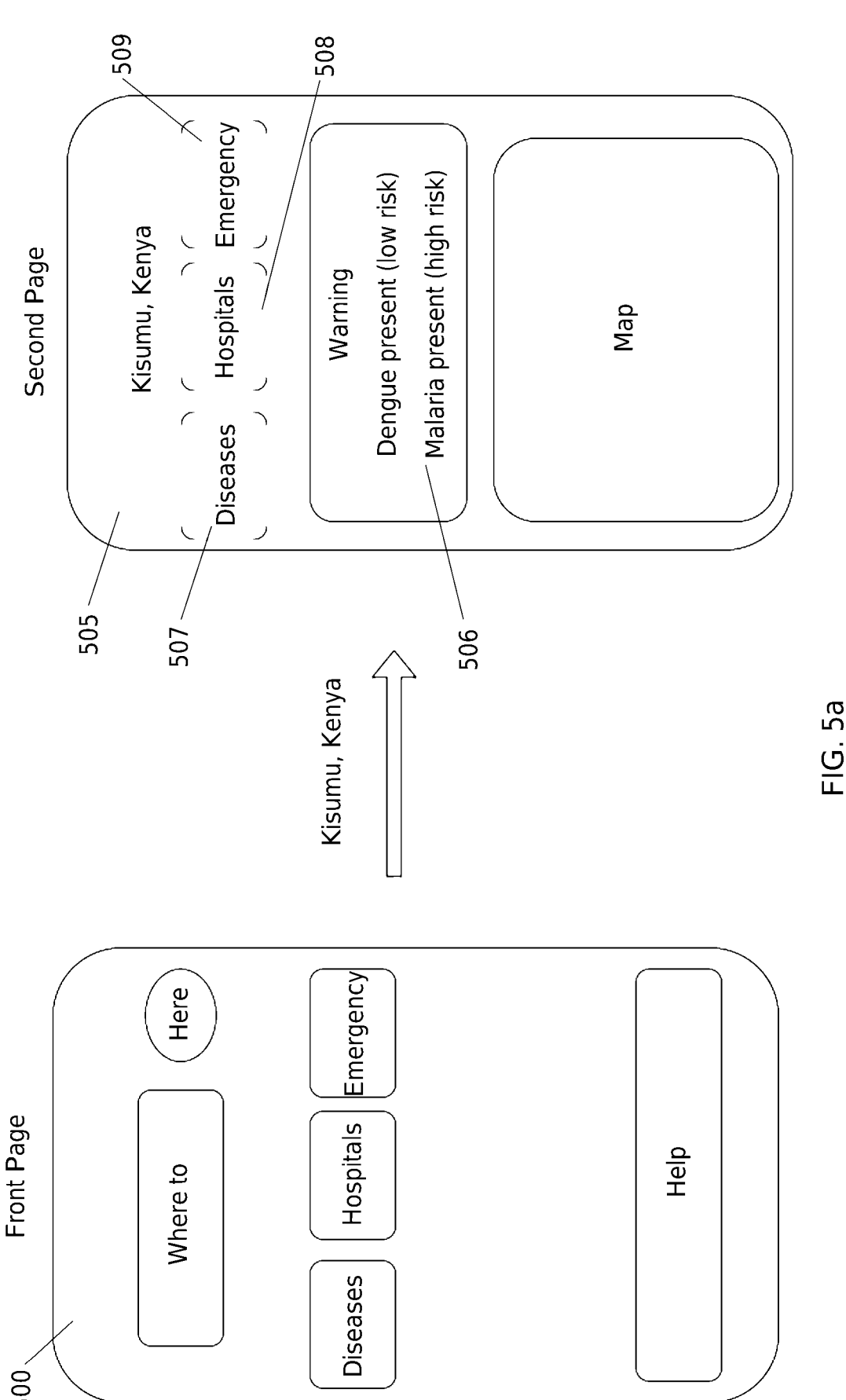
FIGS. 5a-d illustrate screens displayed on the smartphone as it executes the identification of a disease affected area.
Figure 5B:
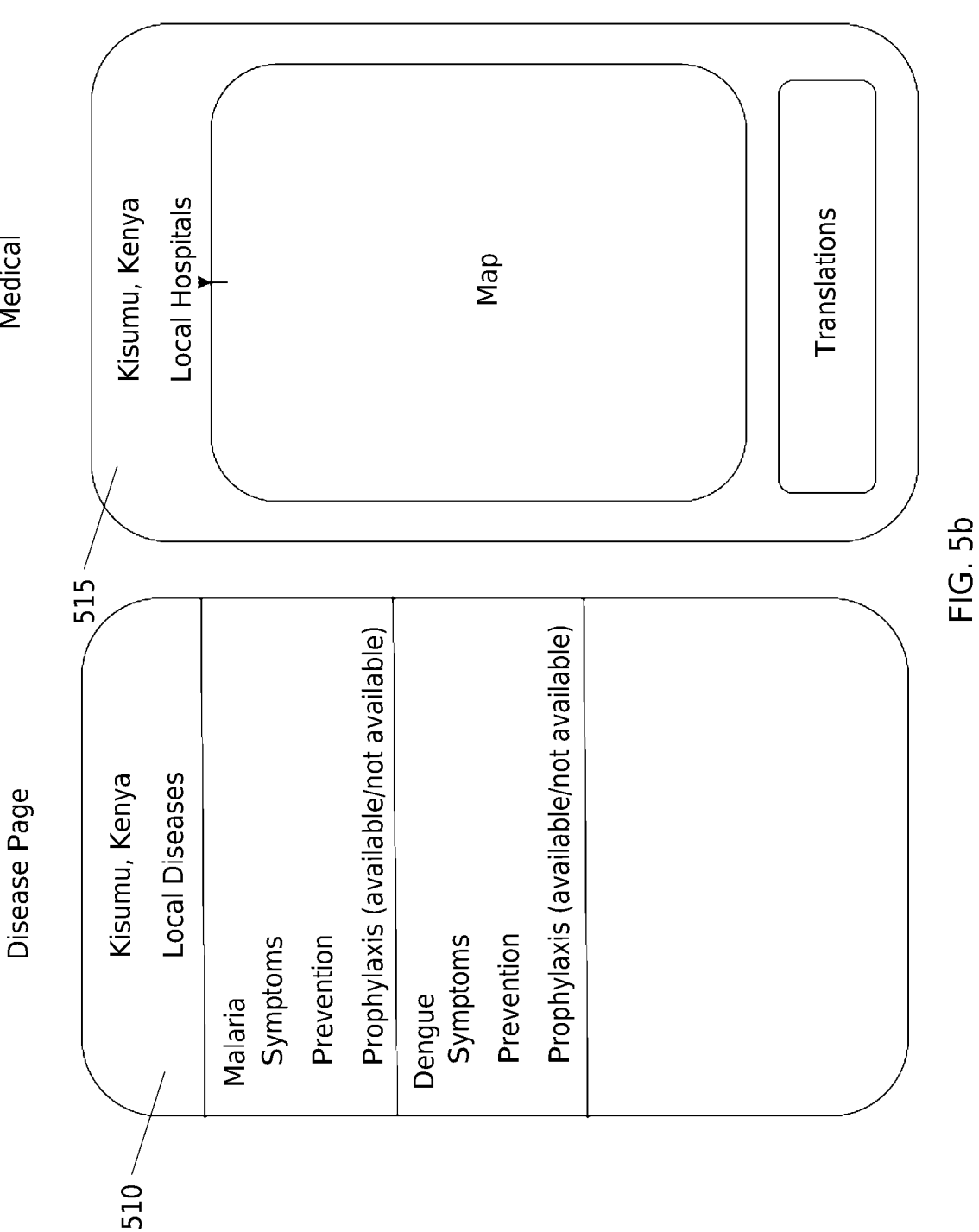
Figure 5D:
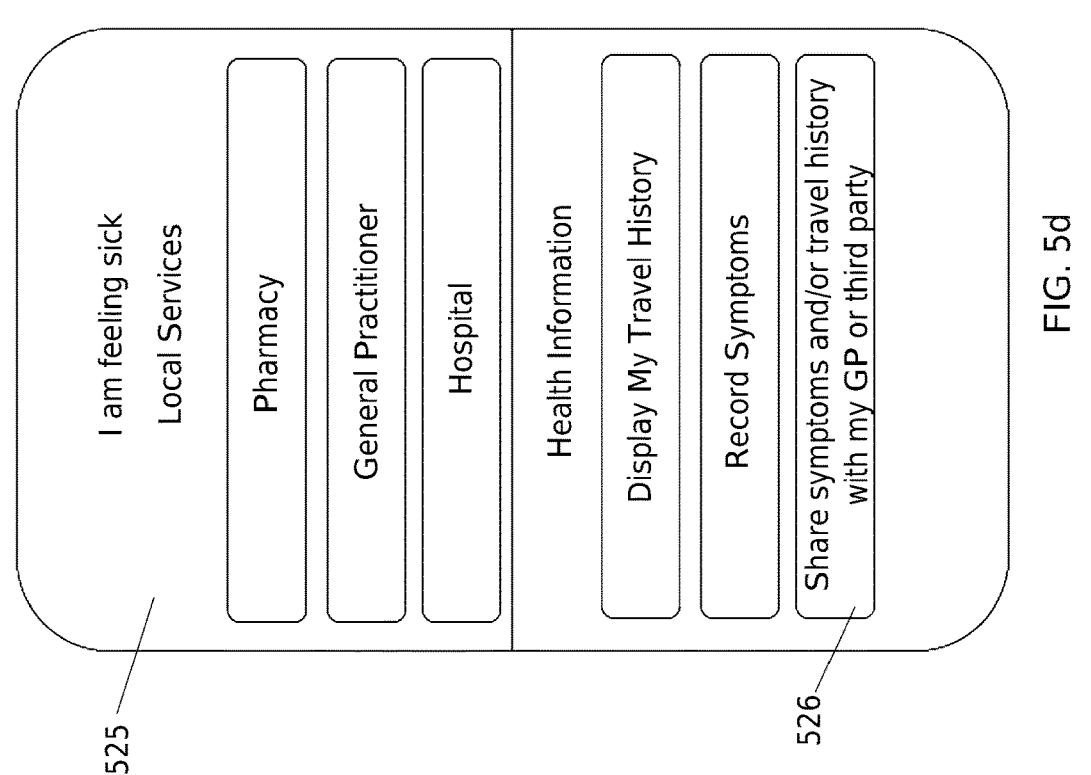
Figure 5C:
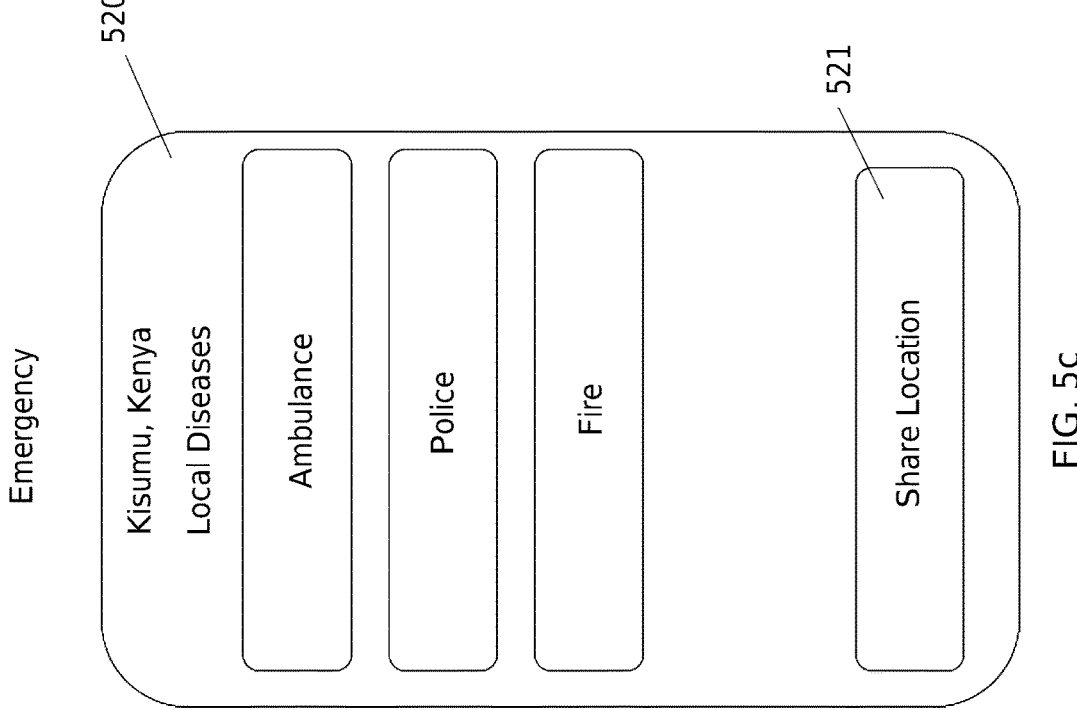

FIGS. 5*a-c* show various screens that are displayed on smartphone 1 as it operates under control of disease warning application 6 to determine current geolocation data and communicate with the server 33 and disease database 20.

Initially, at screen 500 of FIG. 5*a*, the smartphone 1 displays a front page that can be used to select from a number of options. For example, screen 500 allows a user to select from "where to" which acts as a location search feature or "here" which allows a user to assess the disease risk of their current location. After a user selects "here" on screen 500 which, in this example is Kisumu in Kenya, screen 505 is displayed showing a graphical display 506 detailing the risk associated with certain diseases in that area. It is important to recognise that after a user selects "here" on screen 500, the smartphone 1 proceeds to determine a current location using the built-in GPS module and query the disease database as described above.

On screen 505 it can be seen that there are two diseases in the area, these being Malaria, which is categorised as "high risk", and Dengue, which is categorised as "low risk". The risk levels provided herein are only intended to be exemplary and should not be taken as limiting. A range of risk levels may be used (e.g. Absent, present (low risk), present (medium risk), present (high risk), present (extreme risk)) or a completely different categorising system may be used (e.g. colour grade system). The specific category level names are not limited to those in the examples listed above.

Screen 505 also includes a number of buttons that may be clicked by the user to take them to pages containing information on services and diseases. For example, button 507 labelled "Diseases" takes the user to screen 510 of the application on smartphone 1 which provides information on the two diseases listed on screen 505.

In another example, button 508 labelled "Hospitals" takes the user to screen 515 which generates a graphical display of a map of the area on the smartphone 1 highlighting the locations of hospitals in the area.

In operation, the disease warning application 6 described above accesses a database (which may be disease database 20 or a secondary database) containing the name, street address (where available), location and phone number of medical facilities, pharmacies and certified businesses and services, which are then provided on-screen for the user.

When the user requests information about the closest facilities of a particular type (e.g. hospital), the facilities closest to the GPS co-ordinates given will be returned. Directions may also be provided to the selected service.

In some embodiments, the closest relevant services will be displayed in a map, with an option to select by list instead of map.

When a specific service is selected the relevant information will be displayed for the user along with an option to give directions to travel to the destination. For the web-based service, the user will be asked for a point of origin as well as selecting the service. These instructions will then be available to use online or download/print so they can be taken offline and used in areas with unreliable or non-existence cellular service.

In a third example, button 509 labelled "Emergency" takes the user to screen 520 which provides access to emergency services such as an ambulance, police or fire services.

Screen 520 also provides the user with the ability to share the data (e.g. GPS data and relevant disease data) of their disease warning application 6 from their smartphone 1 to a third party device (such as the device of a GP) through button 521 in FIG. 5c or button 526 in FIG. 5d. The shared data can then be used to modify and/or update risk maps.

Figure 4A:
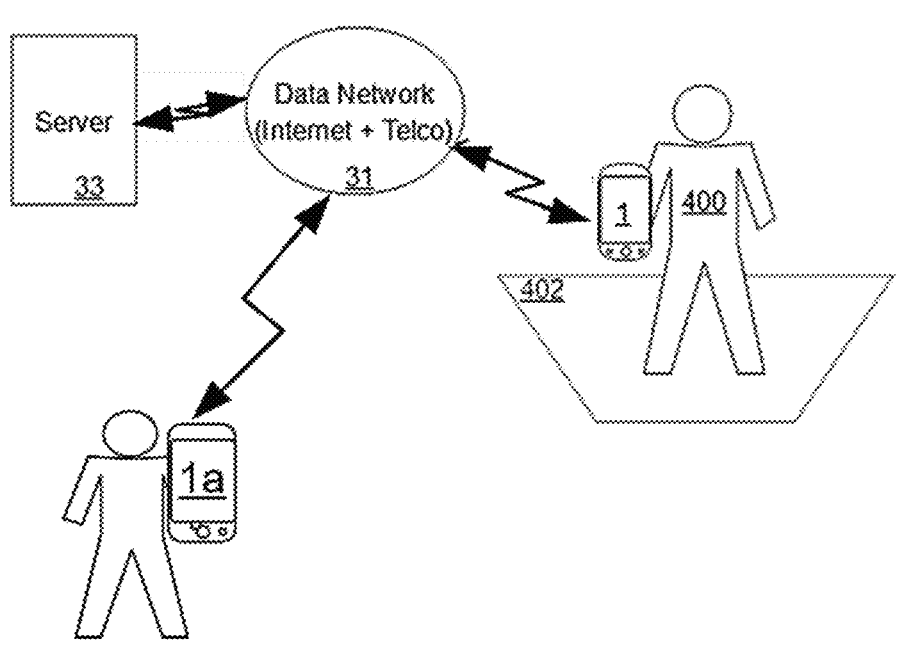

In embodiments where symptom data and/or geolocation data have been shared with a second electronic communication, in the form of second smartphone 1a of a GP 401 in FIG. 4a, the smartphone 1 and second smartphone 1a can communicate via a two-way open communication channel (that is preferably encrypted at both ends). The shared geolocation data comprises current geolocation data and/or previous or historic geolocation data obtained by the GPS module 17 of the smartphone 1 and which has been stored on the smartphone 1 in memory 5. Thus, the user 400 may provide symptom or/or movements updates to the GP 401 and the GP 401 may provide medical advice to the user 400 via the respective smartphones 1, 1a over telecommunication infrastructure and hardware available to the respective smartphones 1, 1a in their respective locations.

Remaining at FIG. 4a, in one particular embodiment, a traveller (i.e. user 400) activates the disease warning application on smartphone 1 which transmits relevant data to smartphone 1a of their nominated medical professional or other third party 401. Data transmitted may include some or all of the following: travel history, recoded symptoms, predicted risk estimates of various diseases, digital medical records (e.g. scanned or photographed records from local medical professionals).

Images of medical records may be digitally translated using algorithms such as but not limited to natural language processing. These electronic health data may be translated via the use of a server or by software on the smartphones 1, 1a.

Upon activation at smartphone 1 by user 400, based on the telecommunication systems available to both parties, text messages, emails or short 'chat' style texts may be transmitted between the two parties. Where possible, direct audio or video communication links may also be established to enable the two parties to communicate both orally or visually.

In a further embodiment shown in FIG. 6, the risk rating may comprise the current risk rating 506 and a future risk rating 506a. The current risk rating 506 is the risk rating generated as described above.

The future risk rating 506a relates to a risk of transmission or infection by a disease in the current geolocation within a predetermined period of time from a current time. For example, the future risk rating 506a relates to a risk of infection by a disease within the next two weeks.

The future risk rating 506a is determined from a predictive model which can take into account multiple factors and datum (such as weather data and movement of people) that are known to impact the ability of a disease, virus, or the like, to spread. For example, heavy rainfall is known to lead to an increase in the mosquito population in the area within approximately two weeks. The increased mosquito population can then lead to an increased risk of transmission of malaria (or other mosquito-borne diseases). Therefore, the weather data can be incorporated into the predictive model and used to calculate the future risk rating 506a which is displayed to the user.

In the event that the user becomes unwell, the GPS data and disease data can be used, along with incubation periods for diseases present in areas which they have visited to predict the risk of illness being caused by each disease they may have encountered. Users can inform the system (through screen 530 of disease warning application 6 shown in FIG. 5d) when they are experiencing symptoms and a list of potential diseases based on symptoms and disease specific incubation periods will be reported. Machine learning is utilised to predict the risk of each potential disease based on GPS travel history and reported symptoms and rank these according to predicted risk in order from highest to lowest.

By querying a disease database using a current location, up-to-date disease warning information can be provided to a traveller in real time thereby allowing the traveller to assess the infection risk to themselves at any time. Furthermore, disease risk can be assessed on an ongoing basis if the traveller is moving between countries, cities or different areas within a city or when they return to their home country.

In another advantage, the difficulty associated with assessing which diseases a traveller may have been exposed to and the likelihood of infection in the event that they become unwell can be drastically reduced through a review of the traveller's movements. In particular, the traveller's movement data can be used to identify disease infected vectors in an area the infected traveller visited. In some embodiments, as the user moves through an area, the system records the geographic coordinates as movement data which may be used to identify common points of infection and/or transmission. Effectively, this allows contact tracing to be performed and models to be derived from the travel data to track infections and possible infections among people and disease vectors.

In another embodiment, the present disclosure provides a method and system for identifying a high-risk environment such as an environment that may be subject to environmental phenomena, such as natural disasters. The system provides an environment database storing environment data associated with one or more geolocations. This is similar to the implementation described above using a disease database. However, the environment database collects and stores data relating to environmental phenomena such as a weather patterns, for example. Live updated alert platforms may be incorporated into the environment database. Data from online sources (e.g. RSS feeds, regularly updated data repositories and, government and non-government websites) pertaining to natural disasters can also be used.

The system also provides an electronic communication device which is adapted to determine a current geolocation of the electronic communication device and for communication with the environment database in much the same way that the electronic communication device communicates with the disease database.

In use, upon detecting the current geolocation of the electronic communication device, the electronic communication queries the environment database to identify one or more environmental phenomena associated with the current geolocation and display a risk rating associated with each of the one or more identified environmental phenomena associated with the current geolocation of the electronic communication device on the display of the electronic communication device.

Data collected and stored in the environment database may include pre-calculated risk maps, time stamped GPS coordinate, data describing current environmental hazards, supplementary information about seasonal environmental phenomena, name, location and contact details of hospitals and pharmacies, local emergency contact numbers, and embassy information (e.g. name, location and contact details of an embassy or ambassador).

Implementations of the invention can be realized as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "computer system" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations of the present disclosure can be realized in a computing system that includes a back end component, e.g., as a data server, or that includes a middleware component, e.g., an application server, or that includes a front end component, e.g., a client computer having a graphical user interface or a Web browser through which a user can interact with an implementation of the present disclosure, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step, etc.

While this disclosure contains many specifics, these should not be construed as limitations on the scope of the disclosure or of what may be claimed, but rather as descriptions of features specific to particular implementations of the disclosure. Certain features that are described in this disclosure in the context of separate implementations can also be provided in combination in a single implementation. Conversely, various features that are described in the context of a single implementation can also be provided in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the present disclosure have been described. Other implementations are within the scope of the following claims. For example, the actions recited in the claims can be performed in a different order and still achieve desirable results.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

The invention claimed is:

1. A method for identifying a disease affected area, the method comprising the steps of:

activating a geolocation device of an electronic communication device;

determining, by the geolocation device, geolocation data comprising a current geolocation of the electronic communication device, wherein the current geolocation is automatically retrieved by a GPS module in the electronic communication device or by a mobile phone tracking process and the geolocation device tracks and stores movement trajectory data over a predetermined time interval to generate historical geolocation data;

querying, by the electronic communication device, a disease database to identify one or more diseases associated with the current geolocation by providing the geolocation data to the disease database, the disease database having disease data comprising one or more georeferenced risk maps, timestamped GPS coordinate data relating to confirmed disease cases, weather data associated with the current geolocation and disease vector data associated with the current geolocation;

identifying, by the electronic communication device, disease vectors based on historical and real-time disease prevalence in the current geolocation of the electronic communication device, wherein the disease vectors are determined by comparing confirmed disease case location stored in the disease database with georeferenced risk maps and updating disease risk models using GPS movement trajectory data and weather data;

combining, by the electronic communication device, the geolocation data obtained in relation to the current geolocation and the disease data;

comparing, by the electronic communication device, the combined geolocation data, and the disease data with incubation periods for diseases present in the current geolocation to predict a risk of illness being caused by each of the identified diseases associated with the current geolocation;

generating, by the electronic communication device, a predictive model incorporating the weather data, presence of disease and movement of people based on the timestamped GPS coordinate data relating to confirmed disease cases from the disease database and the model applies pre-calculated risk maps and real-time GPS movement data to generate an updated disease risk assessment;

calculating, by the electronic communication device, from the updated disease risk assessment an updated risk map and an updated risk rating associated with each of the one or more identified diseases associated with the current geolocation based on the identified disease vectors, the combined geolocation data and the disease data, wherein the updated risk rating comprises a current risk rating and a future risk rating, wherein the future risk rating relates to a risk of transmission or infection in a predetermined period of time from a current time based on the predictive model; and generating a graphical display on a display of the electronic communication device displaying the updated risk map and the risk rating associated with each of the one or more identified diseases associated with the current geolocation.

2. The method of claim 1, wherein the disease database is configured to receive, process and store disease data for one or more geolocations from one or more sources.

3. The method of claim 2, wherein the one or more sources include: pre-calculated risk maps and time stamped global positioning system (GPS) coordinate data.

4. The method of claim 2, wherein the disease database generates georeferenced risk maps from the disease data for one or more geolocations.

5. The method of claim 2, wherein the disease data comprises a risk rating for each of one or more diseases associated with one or more geolocations.

6. The method of claim 2, wherein the disease database calculates the risk rating for each of one or more diseases associated with one or more geolocations.

7. The method of claim 1, wherein the mobile phone tracking process comprises a triangulation process.

8. The method of claim 1, wherein the disease database is remote from the electronic communication device or stored on the electronic communication device.

9. The method of claim 1, wherein the graphical display comprises a push notification or text message displayed on the display of the electronic communication device.

10. The method of claim 9, wherein the push notification or text message comprises the risk rating for each of the one or more identified diseases associated with the current geolocation.

11. The method of claim 1, wherein after determining the current geolocation, the method further comprises the step of determining an updated geolocation of the electronic communication device at predetermined intervals;

querying the disease database from the electronic communication device at each predetermined interval, to identify one or more diseases associated with the updated geolocation; and generating a graphical display on a display of the electronic communication device displaying a risk rating for each of the one or more identified disease risk ratings associated with the updated geolocation.

12. The method of claim 1, wherein the method further comprises the step of transmitting geolocation data and/or symptom data from the electronic communication device to a second electronic communication device.

13. A system for identifying a disease affected area, the system comprising:

a disease database storing disease data associated with one or more geolocations, the disease data comprising one or more georeferenced risk maps, timestamped GPS coordinate data relating to confirmed disease cases, weather data associated with the current geolocation and disease vector data associated with the current geolocation;

an electronic communication device adapted for communication with the disease database, the electronic communication device having a display and a geolocation device for determining a current geolocation of the electronic communication device, wherein the current geolocation of the electronic communication device is automatically determined by a GPS module in the electronic communication device or by a mobile phone tracking process and transmitted as geolocation data and the geolocation device tracks and stores movement trajectory data over a time interval that may be predetermined or dynamically adjusted according to behavioral patterns to generate historical geolocation data;

wherein upon detecting the current geolocation of the electronic communication device, the electronic communication device:

queries the disease database to identify one or more diseases associated with the current geolocation;

identifies disease vectors based on historical and real-time disease prevalence in the current geolocation of the electronic communication device, wherein the disease vectors are determined by comparing confirmed disease case location stored in the disease database with georeferenced risk maps and updating disease risk models using GPS movement trajectory data and weather data;

combines the geolocation data obtained in relation to the current geolocation and the disease data;

compares the combined geolocation data, and the disease data with incubation periods for diseases present in the current geolocation to predict a risk of illness being caused by each of the identified diseases associated with the current geolocation;

generates a predictive model incorporating the weather data, presence of disease and movement of people based on the timestamped GPS coordinate data relating to confirmed disease cases from the disease database and the model applies pre-calculated risk maps and real-time GPS movement data to generate an updated disease risk assessment;

calculating, from the updated disease risk assessment, an updated risk map and an updated risk rating associated with each of the one or more identified diseases associated with the current geolocation based on the identified disease vectors and the combined geolocation data and the disease data, wherein the updated risk rating comprises a current risk rating and a future risk rating, wherein the future risk rating relates to a risk of transmission or infection in a predetermined period of time from a current time based on the predictive model; and display the updated risk map and the updated risk rating associated with each of the one or more identified diseases associated with the current geolocation of the electronic communication device on the display of the electronic communication device.

\* \* \* \* \*